Figure 1:
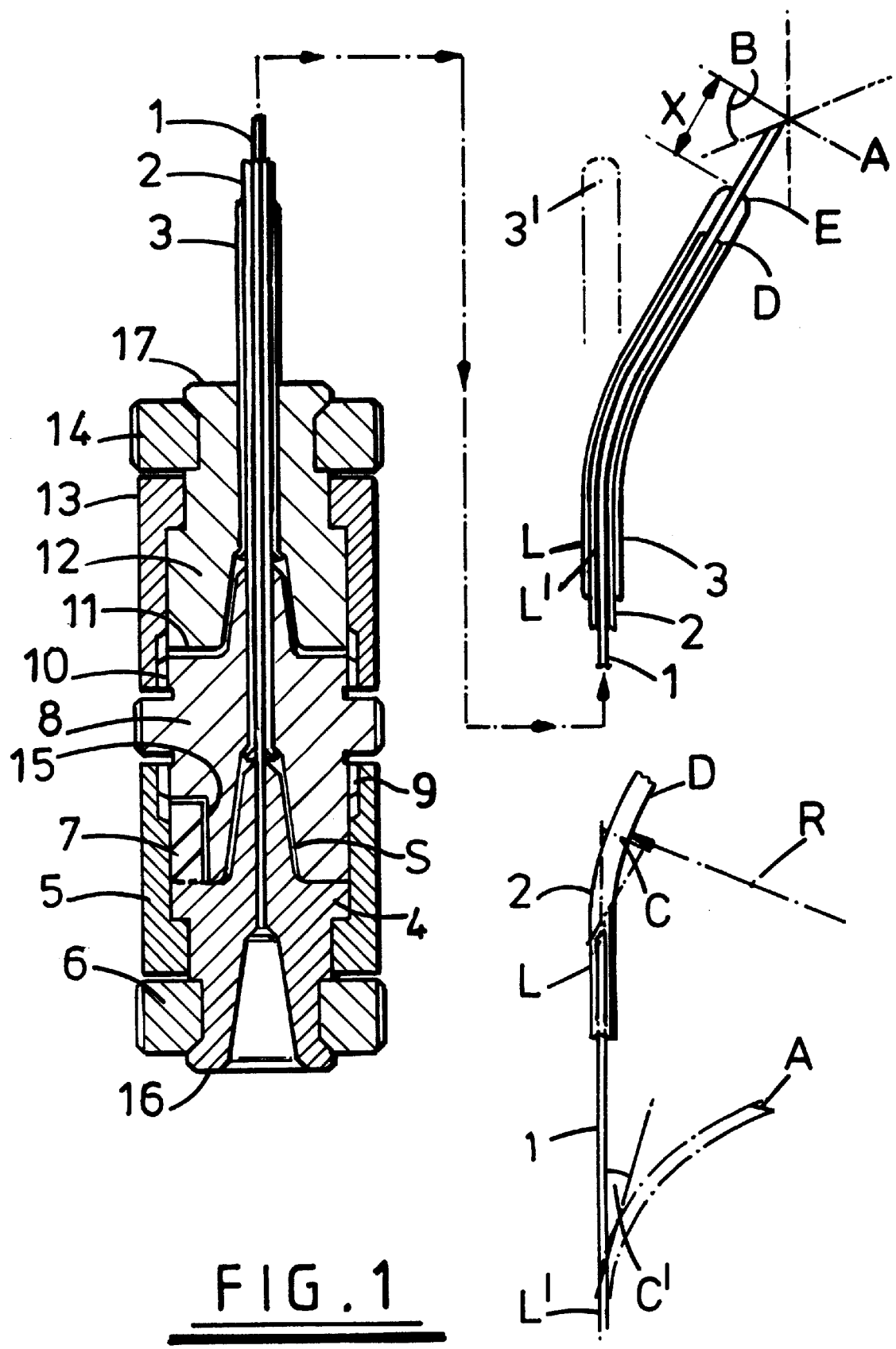

United States Patent [19]
Gould

[11] Patent Number: 5,910,133
[45] Date of Patent: Jun. 8, 1999

[54] TRANSINTIMAL RECANALISATION DEVICE

[76] Inventor: Derek Alan Gould, 52 Dunbabin Road, Liverpool, L16 7QH, United Kingdom

[21] Appl. No.: 08/532,700
[22] PCT Filed: Apr. 13, 1994
[86] PCT No.: PCT/GB94/00781
§ 371 Date: Feb. 12, 1996
§ 102(e) Date: Feb. 12, 1996
[87] PCT Pub. No.: WO94/23785
PCT Pub. Date: Oct. 27, 1994
[51] Int. Cl.$^6$ .................................................. A61M 5/178
[52] U.S. Cl. ........................................... 604/164; 604/272
[58] Field of Search ..................................... 604/164, 165, 604/166, 171, 281, 198, 272

[56] References Cited

U.S. PATENT DOCUMENTS

| | | | |
|---|---|---|---|
| 4,013,080 | 3/1977 | Froning | 128/347 |
| 4,511,356 | 4/1985 | Froning et al. | 604/164 |
| 4,518,383 | 5/1985 | Evans | 604/164 X |
| 5,114,402 | 5/1992 | McCoy | 604/281 X |
| 5,152,749 | 10/1992 | Giesy et al. | 604/164 |

FOREIGN PATENT DOCUMENTS

0269763A1  12/1986  European Pat. Off. .
2124503    8/1983   United Kingdom .

*Primary Examiner*—Ronald Stright
*Assistant Examiner*—A. T. Nguyen
*Attorney, Agent, or Firm*—Woodard, Emhardt, Naughton Moriarty & McNett

[57] ABSTRACT

A transintimal recanalization device comprising a guide tube (2) having a bend (C) in its length, a flexible needle (1) having a bevelled end (A) and a bend (C') in its length and located in said tube (2), wherein said needle (1) is movable from a covered position wherein said bevelled end (A) is within the tube (2) to an uncovered position in which said bevelled end (A) is exposed, and wherein said bends (C, C') match thereby orientating the bevelled end with respect to the tube (2). The device finds particular application in breaking through a vessel intima into a targeted distal vessel lumen in order to allow the passage of a guidewire.

7 Claims, 2 Drawing Sheets

TRANSINTIMAL RECANALISATION DEVICE

DESCRIPTION

This invention relates to an arterial transintimal recanalisation device.

In middle age, over 40% of males have evidence of significant vascular impairment due to arterial fat deposits. This generalised disease, atherosclerosis, may be heralded by relatively minor, but nonetheless disabling, symptoms of lower limb peripheral vascular disease. This may range in presentation from mild intermittent claudication (limp) which may or may not limit lifestyle, to critical ischaemia with rest pain and/or ulceration or gangrene with an associated risk to life and limb. Management involves attention to the presenting clinical problem, which may be acute and necessitate immediate intervention. Surgery has been the mainstay of intervention for some three decades, however minimally invasive management by balloon angioplasty and related techniques has become of rapidly increasing importance.

In these newer procedures a guidewire is inserted percutaneously through an arterial stenosis or occlusion using x-ray control. A balloon is then passed over the guidewire and inflated in the obstructed segment. These procedures are cost effective, very low risk (about 0.4%) and are performed under a local anaesthetic; discomfort is minimal.

Technical failure occurs in about 20% of occlusions treated and is due to failed guidewire passage (due to heavy calcification, vessel perforation or, most commonly, subintimal passage of the guidewire), elastic recoil of the arterial wall, or acute occlusion due to spasm or thromboembolism. Elastic recoil and acute occlusion can be managed by alternative techniques. Where there has been subintimal guidewire passage, success may necessitate breaking through the intima into the patent, distal lumen. Whilst this can be attained in about 50% of cases in the remainder the intima resists attempts to pass a guidewire through its substance due to a combination of the strength and integrity of the intima and the necessarily atraumatic construction of the guidewires used in these procedures.

An aim of the present invention is to provide a transintimal recanalisation device which overcomes the problem of the intima resisting passage of a guidewire through its substance.

A further aim of the present invention is to provide a method of assembling a transintimal recanalisation device.

In accordance with a first aspect of the present invention there is provided a flexible transintimal recanalisation device adapted to be guided through the vasculature of a patient comprising a guide tube, a flexible needle having a bevelled end and located in said tube, wherein said needle is movable from a covered position wherein said bevelled end is within the tube to an uncovered position in which said bevelled end is exposed, and means enabling said bevelled end to adopt a desired orientation with respect to the tube.

Preferably, said tube has a bend in its length and the needle has a bend in its length which conforms with the bend of the tube, thereby orientating the bevelled end with respect to the tube.

It is preferred that said needle is hollow. Preferably, said device further comprises means for manoeuvering the needle with respect to the tube.

The means for enabling said bevelled end to adopt a desired orientation with respect to the tube may be provided by said manoeuvering means.

In a preferred embodiment of the invention said manoeuvering means comprises a first body connected to an end of the needle spaced from the bevelled end. Preferably said first body is provided with a first aperture therethrough in communication with said hollow needle.

It is preferred that said device further comprises a second body connected to an end of said tube and wherein said second body is provided with a first aperture therethrough to allow the passage of said needle.

Said first body may be provided with a second aperture extending from said first aperture to a surface of the body. Similarly, said second body may be provided with a second aperture extending from said first aperture to a surface of the body.

Said first and second bodies may be provided with cooperating alignment means whereby cooperation of said means results in the bevelled end of the needle adopting a desired orientation.

Preferably, said alignment means comprises a cooperating protrusion and recess.

In a preferred embodiment of the invention, said first and second bodies have means for indicating the relative position of the bevelled end of the needle with respect to an end of the tube spaced from said second body.

Said indicating means may be provided by the cooperation of a protrusion with one of at least two spaced apart apertures.

The first and second bodies preferably form a luer arrangement.

It is preferred that said needle and/or said tube is or are formed from a material having shape memory properties such that the needle or tube will adopt said bend at a given temperature. The material may be a nickel titanium alloy.

In accordance with a second aspect of the present invention there is provided a method of assembling a flexible transintimal recanalisation device adapted to be guided through the vasculature of a patient having a guide tube, a flexible needle having a bevelled end and located in said tube, a body connected to an end of the needle spaced from said bevelled end and means enabling the bevelled end to adopt a desired orientation with respect to the tube wherein said method comprises the steps of threading the end of the needle spaced from said bevelled end through the guide tube until it extends beyond an end of the tube and connecting said body to the end of the needle.

The advantage of this 'back-loading' method is that it enables the device to be assembled without the need to pass the bevelled end of the needle through the length of the tube and hence reduces the risk of the bevelled end being damaged during assembly.

According to a third aspect of the invention there is provided a method of assembling a flexible transintimal recanalisation device adapted to be guided through the vasculature of a patient having a guide tube with a bend in its length, a flexible hollow needle having a bevelled end and located in said tube and means enabling the bevelled end to adopt a desired orientation with respect to the tube wherein said method comprises the steps of threading a stylette into the tube until an end of the stylette extends beyond the bevelled end of the needle, inserting the needle and stylette into the tube until a desired position is reached and withdrawing the stylette.

Once the device has been assembled it may no longer be possible to disconnect the body from the needle and hence if the needle is removed, for example, in order to be cleaned, it will not be possible to reassemble the device by the above-mentioned 'back-loading' method. In consequence, the above method is particularly advantageous since it enables the device to be reassembled with a degree of protection for the bevelled end of the needle which passes through the length of the tube.

Figure 2:
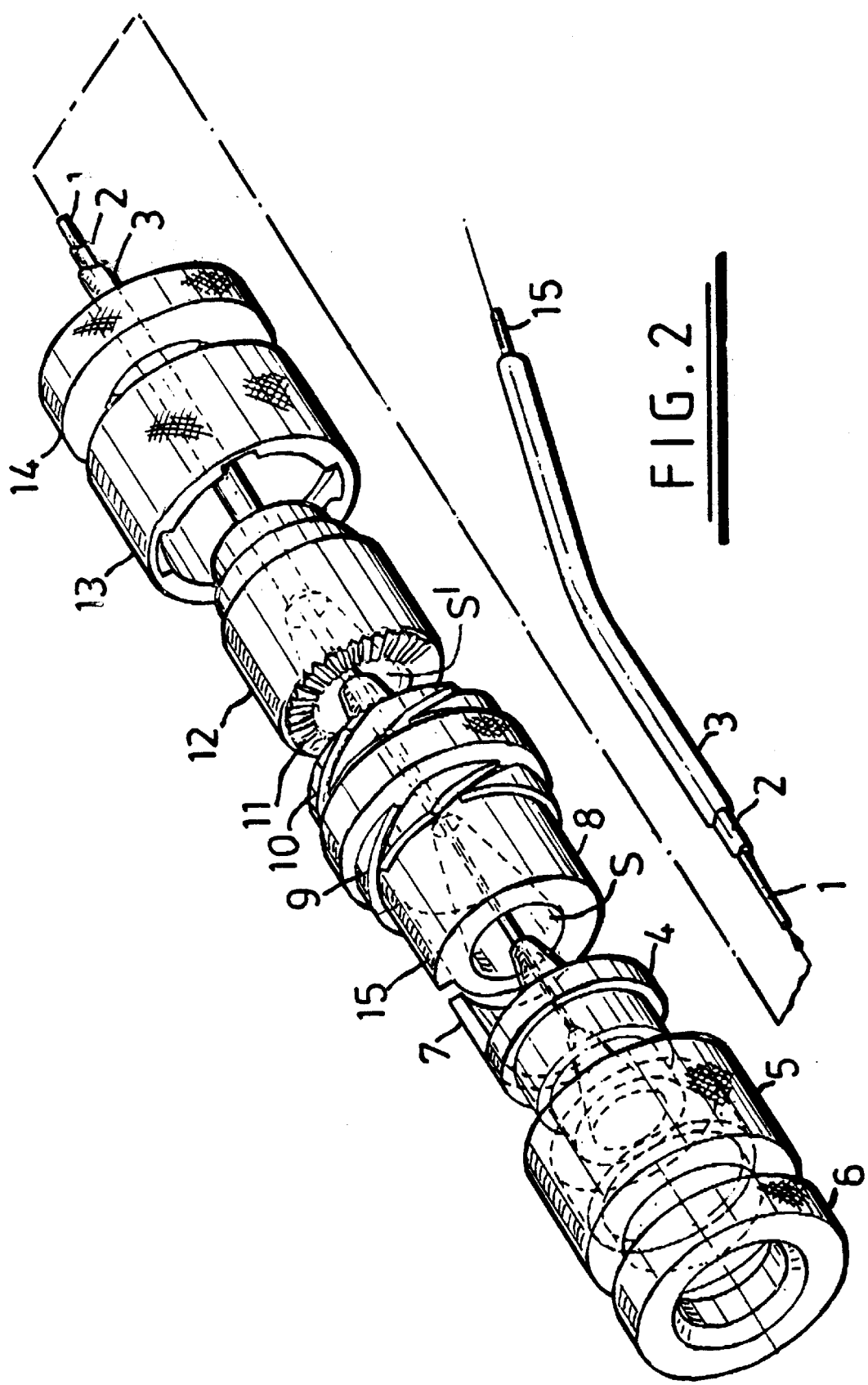

An embodiment of the present invention will now be described, by way of example only, with reference to the accompanying drawings, wherein:

FIG. 1 is a sectioned elevation through the principle components of a device according to the invention; and FIG. 2 is an exploded pictorial illustration of the principle components of the device shown in FIG. 1.

The outer catheter 3 (FIGS. 1 and 2). This is of polyamide or other radiopaque, plastic construction, is tapered to a catheter endhole of in the region of 0.95 mm for passage over a conventional, wound 0.9 mm or similar guidewire. Length of 3 is dependent on the vessel involved, generally 65 cms. Diameter should be in the region of 1.67 mm (5 French).

At the proximal end is a hub 12 with luer sized syringe fitting S' in FIG. 2 and a locking, free rotating collar 13 in FIGS. 1 and 2. The hub construction is such that it is possible to insert the curved end section of 2 through S' and into 3. 3 is normally straight (as shown by 3', FIG. 1) but will adopt a curved end section when the curved end section LD on 2 is fully assembled to 3 (illustrated in FIG. 1).

The guide tube 2 (FIGS. 1 and 2). This is of flexible, radiopaque metal such as nickel titanium. Diameter is dependent on 1 and 3 but generally is in the region of 1 mm (3 French). The length of 2 is such that tip D of 2 lies approximately 0.5 mm behind tip E of 3 when 2 is assembled to 3. The shaft of 2 is straight apart from the end section LD in FIG. 1 which has a curved angulation C which is equivalent in radius of curvature R to curved angulation C' on 1, as in FIG. 1. The length LD on 2 is in the region of 4.5 mm less than the length L'A on curved end section of 1 (i.e. length LD on 2 is of the order of 1.5 to 2 cms). The curved end section LD on 2 commences at L on 2 such that when 1 is fully assembled and advanced into 2, point L on 2 coincides with point L' on 1 where L' is the point of commencement of the curved end section L'A on 1.

The proximal end of 2 is fitted with a hub 8 in FIGS. 1 and 2 with screw fittings 9 and 10 which accommodate locking collars 5 on 1 and 13 on 3, in FIGS. 1 and 2. There is a luer sized syringe fitting S within hub 8 as in FIG. 2. A friction coupling 11 prevents rotation between 12 and 8 when these parts are mated.

The inner needle 1 (FIGS. 1 and 2). This is a flexible needle constructed of a radiopaque metal such as nickel titanium. The length of 1 is such that tip A of 1 projects approximately 4 mms, X in FIG. 1, beyond the tip E of catheter 3 when the transintimal recanalisation device is assembled with the bushes 4 on 1, 8 on 2 and 12 on 1 in FIG. 2 fully mated.

The shaft of 1 is straight apart from end section L'A on 1 which is normally curved as shown by 1' in FIG. 1. The radius of curvature R of end section L'A of 1 is equivalent to that of curved end section LD of 2 in FIG. 1. The length L'A on 1 is in the region of 4.5 mm greater than length LD on 2 (i.e. length L'A is of the order of 1.95 to 2.45 cms). The curved end section L'A on 1 commences at ' on 1 such that when 1 is fully assembled and advanced into 2, point L' on 1 coincides with point L on 2 where L is the point of commencement of the curved end section LD on 2. In this situation (fully assembled), the curved end sections L'A on 1 and LD on 2 coincide, constraining the curved end section L'A on 1 to adopt its lowest energy level and ensuring a constant orientation of bevel B as in FIG. 1. In this fully assembled arrangement, tip A of 1 lies approximately 4.5 mm beyond tip D of 2.

Diameter is such that 1 will pass through 2 with about 0.05 mm clearance and is of the order of 0.64 mm (23 SWG). A low friction coating of inner needle 1 may be utilised. The inner lumen of 1 will allow passage of a 0.38 mm, or similar, guidewire.

The proximal fitting of 1 is a hub 4 in FIGS. 1 and 2 with a luer sized syringe fitting 16 in FIG. 2 and with a single orientation device 7 which, when fully engaged with 15 in FIGS. 1 and 2 and fixed using the collar 5, ensures that the curved end sections of 2 and 1 coincide both longitudinally (i.e. in start points L and L' of curved end sections L and L'A) and in radial orientation. In this situation there is a known orientation of bevel B to the hubs 4 and 8 in FIG. 1. Marks or shape features (not illustrated) on the outer periphery of 6 and 8 may help to achieve this. Rotation between the fully assembled hubs 4 and 8 in FIGS. 1 and 2 may be minimised by use of a friction coupling (not illustrated).

The engagement of single orientation device 7 with 15 in FIGS. 1 and 2 takes place over a distance slightly greater than the length X in FIG. 1 (approx 6 mms) and during this engagement there are two palpable clicks generated by pips on one plastic member corresponding with detents on the other (not illustrated). The first of these palpable clicks occurs when the tip A of 1 lies in its retracted position, about 1 mm behind the distal end D of 2. The second occurs when 1 is fully extended such that tip A of 1 lies approximately 4.5 mms beyond tip D of 2.

Alternatively, provision of an increased number of pips and detents will generate multiple clicks (or clickstops) throughout the extension process, indicating various positions of the needle tip up to full extension.

The hub assemblies 4, 8 and 12 on items 1, 2 and 3 in FIGS. 1 and 2 could be provided with side injection ports (not illustrated) to allow intraprocedural flushing with, eg., heparinised saline.

The advancement of the needle 1 will produce a resultant force on the tip A of 1 due to the constant orientation of B as in FIG. 1. This vector tightens radius of curvature R on the extruded length DA of end section L'A on 1 in FIG. 1 and assists tracking of the needle tip A towards and into the adjacent vessel lumen. In the fully extended position of 1, the angular direction of the tip A of 1 is constantly orientated by the engagement of hub items 7 and 15 in FIGS. 1 and 2 and is indicated by the visual marks and/or tactile features on the outer periphery of 6 and 8.

Guide tube 2 and inner needle 1 are normally supplied preassembled as the puncture device. During manufacture the puncture device may be assembled by back-loading the needle component 1 into guide tube 2 prior to the fitting of hub 4 to needle component 1 in FIGS. 1 and 2. Back-loading will minimise frictional effects of inner wall of guide tube 2 on tip A of 1 during assembly.

An alternative approach to the reduction of frictional effects during assembly could utilise the known shape memory properties of nickel titanium to achieve temperature dependent straightening of curved end sections LD on 2 and L'A on 1 prior to mating these components.

The puncture device is supplied with hub items 7 on 1 and 15 on 2 in FIGS. 1 and 2 pre-engaged at the first clickstop position and with collar 5 of 1 in FIGS. 1 and 2 fully slackened. In this situation, the tip A of inner needle 1 will be in its retracted position within guide tube 2. A detachable safety spacer (not illustrated) could be incorporated between hub items 7 on 1 and 15 on 2 in FIGS. 1 and 2 to prevent premature exposure of tip A of 1 from the puncture device.

Stylette (not illustrated). This optional accessory is a metal, rounded tip stylette of diameter approximately 0.38 mm and with a proximal hub fitting. Length is such that when fully assembled to 1, stylette protrudes beyond tip A of 1 by about 0.6 cm and produces a straightening effect on curved end section L'A of 1.

Whilst 1 and 2 will normally be supplied reassembled, if during use they are separated (for example for cleaning and flushing) and require reassembly, this may be assisted by assembly of stylette to 1, the resulting partial straightening effect on curved end section L'A on 1 assisting re-introduction of the tip A through hub 8 and into the lumen 2, the stylette also reducing impaction of the needle tip A of 1 against the inner wall of 2. Hub item 7 of 1 is then engaged into hub item 15 of 2, at the first clickstop position and the stylette removed, when tip A of 1 will be in its retracted position within guide tube 2.

Where shape memory properties are utilised in construction of guide tube 2 and inner needle 1, temperature dependent straightening of the curved end sections LD on 2 and L'A on 1 would facilitate reassembly of these items.

An ultrasonic doppler stylette (not illustrated). This may be provided to assist needle placement into the vessel lumen by detecting the doppler shift of flowing blood when the needle tip is directed towards a patent vessel lumen.

Use of shape memory properties of nickel titanium. The use of nickel titanium in construction of guide tube 2 and inner needle 1 would permit exploitation of the known shape memory properties of this material. The achievement of temperature dependent straightening of the curved end sections LD on 2 and L'A on 1 in the assembled puncture device would facilitate assembly of the puncture device to catheter 3 in FIG. 1. On attaining normal body temperature (37° C.) the end sections LD on 2 and L'A on 1 would regain their original curved configuration as shown by radius of curvature R in FIG. 1.

Inner guidewire (not illustrated). This is of the order of 0.38 mm diameter. Length is in the region of 160 cms. Low friction coating will assist wire passage.

Inner recanalisation catheter (not illustrated). This final component is a plastic catheter of external diameter about 1 mm (3 French) to allow passage through the lumen of 3 and tapered to an end hole of in the region of 0.43 mm, to fit the inner guidewire used through the lumen of 1. The inner recanalisation catheter will be in the region of 5 cms longer than 3. The hub of this catheter could be constructed to mate the hub and rotating collar 13, 12 of 3 in FIGS. 1 and 2 to passage as one unit.

The mode of use will now be described with the aid of drawings, FIGS. 1 and 2.

A conventional angioplasty will have been attempted but guidewire passage will have failed owing to a persistently subintimal position of the wire. The initial arterial puncture should be made obliquely, a perpendicular puncture may preclude introduction of item 2. The guidewire tip is positioned, under x-ray control, adjacent to the patent distal vessel lumen and in a subintimal position. The catheter used up to this point is removed and replaced over the guidewire by a short, standard, angiographic sheath of internal diameter at least 0.167 mm (0.5 Fr) in excess of the outside diameter of 3, leaving the guidewire in position.

The transintimal recanalisation device is supplied sterile, in sealed packaging and is a single use device. The inner needle 1 and guide tube 2 are normally supplied preassembled as the puncture device. A stylette may be supplied to facilitate reintroduction or 1 into 2 should these items be separated during use. Alternatively, the use of shape memory properties could be used to facilitate reassembly of the puncture device.

The outer catheter 3 is flushed and loaded onto the guidewire and advanced through the sheath to the guidewire tip. The guidewire is removed.

The preassembled puncture device is examined to ensure that the tip A of inner needle 1 is in its retracted position with hub items 7 and 15 on FIGS. 1 and 2 engaged to the first clickstop and tip A of inner needle 1 lying unexposed, within tip D of guide tube 2. Collar 5 in FIG. 2 should be fully slackened. The central lumen of 1 is flushed with heparinised saline introduced through luer fitting 16 of hub 4 of 1 and the puncture device is passed with care through the lumen of catheter 3, assisted if necessary by gentle rotation. Exploitation of the shape memory properties of nickel titanium would allow use of temperature dependent straightening of the curved end sections LD on 2 and L'A on 1 to further facilitate passage of the puncture device through the lumen of catheter 3.

It is essential that during the introduction of the puncture device into catheter 3 the operator ensures that inner needle 1 remains in the retracted position as shown by hub items 7 and 15 in FIGS. 1 and 2 remaining in their first clickstop position. Hubs 12 and 8 in FIGS. 1 and 2 are now locked together using collar 13.

A digital subtraction road map is made using contrast injection into the sheath and with the x-ray tube positioned to show the tip of the assembled device adjacent to and, in the plane imaged, maximally separated from the distal lumen. The curved end section of the assembled device can now be finely directed by gentle rotation of the hub assembly, assisted by the external marks or shapes on the hub assembly. Further contrast injections through the sheath may be necessary during this process, until fluoroscopy in two planes shows the tip of the assembled device to appear directed exactly at the patent, distal vessel lumen and separated from it only be the intimal layer. This process may be further refined by use of an optional ultrasonic stylette which uses a doppler signal to assist direction of the needle. When the angulated tip of the device is judged to be directed at the distal vessel lumen and separated from it by not more than 1 to 2 mms, the safety spacer (if fitted between hub items 7 and 15 in FIGS. 1 and 2) is removed and the hub 4 of 1 is advanced to the second clickstop of hub items 7 and 15, shown in FIGS. 1 and 2. This advances the tip A of 1 through the intimal layer to a position approximately 4 mm, X in FIG. 1, beyond the tip E in FIG. 1 of catheter 3 and into the distal vessel lumen. Collar 5 of 1 is now fully secured to male component 9 on hub 8 of 2 in FIGS. 1 and 2. (An arrangement of 7 and 15 in FIGS. 1 and 2 may be utilised whereby there are multiple clickstops (not illustrated) indicating varying degrees of extension of tip A of 1).

If there is free return of arterial blood through the hub assembly, 0.38 mm (or similar) guidewire passage can now be attempted. Alternatively, a small contrast injection can be made through the lumen of 1 via hub 16, FIG. 1, to determine the position of A, FIG. 1. If tip A placement is not satisfactory, the collar 5 on hub 4 in FIGS. 1 and 2 is slackened allowing the inner needle tip A to be withdrawn into the retracted position (first clickstop position of 7 and 15 in FIGS. 1 and 2). Following careful repositioning of the transintimal recanalisation device as above, further attempts may be made to enter the lumen. The small diameter of 1 reduces the risks of damage to collateral vessels and target vessel perforation. It is however stressed that significant force must not be used and the procedure must not be progressed if the inner needle tip A is not within the distal vessel lumen.

Where the position of tip A of 1 is judged satisfactory, the 0.38 mm guidewire is advanced beyond tip A of 1, with gentle torque if necessary, and into the distal vessel lumen. Passage of the wire is facilitated by the constant orientation distally, as B in FIG. 1 of the needle bevel. When the 0.38 mm wire position is judged satisfactory, collar 13 on hub 12 of catheter 3 in FIG. 2 is released and the puncture device, comprising inner needle 1 and guide tube 2 secured together by collar 5 of hub 4, is removed over the wire as one unit and without withdrawing either catheter 3 or the wire.

It should usually be possible to now advance catheter 3 over the 0.38 mm wire and into the target vessel lumen. This process may be facilitated by use of an inner, coaxial, recanalisation catheter (not illustrated) which is passed over the wire, through the outer catheter 3. The inner recanalisation catheter, if used, is longer than catheter 3, allowing passage of inner recanalisation catheter into the distal lumen over the 0.38 mm wire. Outer catheter 3 is then advanced over combined wire/inner catheter until tip of 3 lies in the distal vessel lumen.

The inner catheter and 0.38 mm guidewire are now removed and contrast injection can be performed to confirm the position of 3 in the distal vessel lumen.

If position of 3 is judged to be satisfactory, a 0.86 mm guidewire can be inserted and 3 exchanged for a conventional balloon catheter for angioplasty to be performed in the standard manner.

I claim:

1. A transintimal recanalisation device comprising:

a guide tube having a bend in its length, a flexible hollow needle having a bevelled end and located in said tube, wherein said needle is movable from a covered position wherein said bevelled end is within the tube to an uncovered position in which said bevelled end is exposed and has a bend in its length which conforms with the bend in the tube thereby enabling said bevelled end to adopt a desired orientation with respect to the tube;

means for manoeuvering the needle with respect to the tube, said manoeuvering means including a first body connected to an end of said needle spaced from the bevelled end, said first body having a first aperture therethrough in communication with said needle;

a second body connected to an end of said tube wherein said second body is provided with a first aperture therethrough to allow the passage of said needle;

wherein said first or second body has a second aperture extending from said first aperture to a surface of the body; and wherein said first and second bodies are provided with cooperating alignment means whereby cooperation of said means results in the bevelled end of the needle adopting a desired orientation, said alignment means including a cooperating protrusion and recess; and said first and second bodies further including means for indicating the relative position of the bevelled end of the needle with respect to an end of said tube spaced from said second body; and, wherein said indicating means is provided by the cooperation of a protrusion with one of at least two spaced apart apertures.

2. A device as claimed in claim 1, wherein said first and second bodies form a luer arrangement.

3. A device according to claim 2, wherein said needle or said tube is or are formed from a material having shape memory properties such that the needle or tube will adopt said bend at a given temperature.

4. A device as claimed in claim 3, wherein said material is a nickel titanium alloy.

5. A method of assembling a flexible transintimal recanalisation device adapted to be guided through the vasculature of a patient having a guide tube (2), a flexible needle (1) having a bevelled end (A) and located in said tube (2), a body (4) connected to an end of the needle (1) spaced from said bevelled end (A) and means for enabling the bevelled end (A) to adopt a desired orientation with respect to the tube (2) wherein said method comprises the steps of threading the end of the needle (1) spaced from said bevelled end (A) through the guide tube (2) until it extends beyond an end of the tube (2) and connecting said body (4) to the end of the needle (1).

6. A method of assembling a transintimal recanalisation device having a guide tube with a bend in its length, a flexible hollow needle having a bevelled end and located in said tube and means for enabling the bevelled end to adopt a desired orientation with respect to the tube wherein said method comprises the steps of threading a stylette into the needle until an end of the stylette extends beyond the bevelled end of the needle, inserting the needle and stylette into the tube until a desired position is reached and withdrawing the stylette.

7. A transintimal recanalisation device comprising:

a guide tube having a bend in its length, a flexible hollow needle having a bevelled end and located in said tube, wherein said needle is movable from a covered position wherein said bevelled end is within the tube to an uncovered position in which said bevelled end is exposed and has a bend in its length which conforms with the bend in the tube thereby enabling said bevelled end to adopt a desired orientation with respect to the tube, wherein said needle or said tube is formed from a material having shape memory properties such that the needle or tube will adopt said bend at a given temperature;

means for manoeuvering the needle with respect to the tube, wherein said manoeuvering means includes a first body connected to an end of the needle spaced from the bevelled end;

a second body connected to an end of said tube and wherein said second body is provided with a first aperture therethrough to allow the passage of said needle;

wherein said first and second bodies have means for indicating the relative position of the bevelled end of the needle with respect to an end of the tube spaced from said second body; and wherein said indicating means is provided by the cooperation of a protrusion with one of at least two spaced apart apertures.

* * * * *